US00PP26279P2

(12) United States Plant Patent
Dummen

(10) Patent No.: US PP26,279 P2
(45) Date of Patent: Dec. 29, 2015

(54) ***EUPHORBIA* PLANT NAMED 'DUESTASUFLA'**

(50) Latin Name: *Chamaesyce hypericifolia*
Varietal Denomination: Duestasufla

(71) Applicant: Tobias Dummen, Rheinberg (DE)

(72) Inventor: Tobias Dummen, Rheinberg (DE)

(73) Assignee: Dümmen Group B.V., DeLier (NL)

( * ) Notice: Subject to any disclaimer, the term of this patent is extended or adjusted under 35 U.S.C. 154(b) by 189 days.

(21) Appl. No.: 13/987,103

(22) Filed: Jul. 1, 2013

(51) Int. Cl.
*A01H 5/02* (2006.01)

(52) U.S. Cl.
USPC ..... Plt./302

(58) Field of Classification Search
USPC ..... Plt./302, 263.1
See application file for complete search history.

(56) References Cited

PUBLICATIONS

New Annuals, Perennials, Woody Plants and Roses: Hitting in 2013. Landscape Trades Nov.-Dec. 2012, vol. 34, No. 9, pp. 6-20.*

* cited by examiner

*Primary Examiner* — June Hwu
(74) *Attorney, Agent, or Firm* — C. A Whealy

(57) ABSTRACT

A new and distinct cultivar of *Euphorbia* plant named 'Duestasufla', characterized by its compact, upright, outwardly spreading and mounding plant habit; moderately vigorous growth habit; freely branching habit; and numerous and relatively large inflorescences white-colored flower bracts.

1 Drawing Sheet

Botanical designation: *Chamaesyce hypericifolia.*
Cultivar denomination: 'DUESTASUFLA'.

BACKGROUND OF THE INVENTION

The present invention relates to a new and distinct cultivar of *Euphorbia* plant, botanically known as *Chamaesyce hypericifolia* and hereinafter referred to by the name 'Duestasufla'.

The new *Euphorbia* plant is a product of a planned breeding program conducted by the Inventor in Rheinberg, Germany. The objective of the breeding program is to create new compact and freely branching *Euphorbia* plants with numerous large inflorescences.

The new *Euphorbia* plant is a naturally-occurring whole plant mutation of a proprietary selection of *Chamaesyce hypericifolia* identified as code number EW09-0599-0030, not patented. The new *Euphorbia* plant was discovered and selected by the Inventor as a single flowering plant from within a population of plants of the parent selection in a controlled greenhouse environment in Rheinberg, Germany in May, 2012.

Asexual reproduction of the new *Euphorbia* plant by vegetative tip cuttings in a controlled greenhouse environment in Rheinberg, Germany since June, 2012 has shown that the unique features of this new *Euphorbia* plant are stable and reproduced true to type in successive generations.

SUMMARY OF THE INVENTION

Plants of the new *Euphorbia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Duestasufla'. These characteristics in combination distinguish 'Duestasufla' as a new and distinct *Euphorbia* plant:

1. Compact, upright, outwardly spreading and mounding plant habit.
2. Moderately vigorous growth habit.
3. Freely branching habit.
4. Numerous and relatively large inflorescences white-colored flower bracts.

The new *Euphorbia* can be compared to plants of the parent selection. Plants of the new *Euphorbia* differ primarily from plants of the parent selection in inflorescence size as plants of the new *Euphorbia* have larger inflorescences than plants of the parent selection. In addition, plants of the new *Euphorbia* are more freely branching than plants of the parent selection.

Plants of the new *Euphorbia* can also be compared to plants of *Euphorbia hypericifolia* 'Silverfog', disclosed in U.S. Plant Pat. No. 20,858. In side-by-side comparisons, plants of the new *Euphorbia* differed from plants of 'Silverfog' in the following characteristics:

1. Plants of the new *Euphorbia* were more compact than plants of 'Silverfog'.
2. Plants of the new *Euphorbia* had smaller and darker green-colored leaves than plants of 'Silverfog'.
3. Plants of the new *Euphorbia* had larger inflorescences than plants of 'Silverfog'.

BRIEF DESCRIPTION OF THE PHOTOGRAPH

The accompanying colored photograph illustrates the overall appearance of the new *Euphorbia* showing the colors as true as it is reasonably possible to obtain in colored reproductions of this type. Colors in the photograph may differ slightly from the color values cited in the detailed botanical description which accurately describe the colors of the new *Euphorbia* plant.

The photograph is a side perspective view of a typical flowering plant of 'Duestasufla' grown in a container.

DETAILED BOTANICAL DESCRIPTION

The aforementioned photograph and following observations, measurements and values describe plants grown during the summer in 12-cm containers in a glass-covered greenhouse in Rheinberg, Germany and under cultural practices typical of commercial *Euphorbia* production. During the production of the plants, day and night temperatures averaged 22° C. and light levels averaged 4,500 lux. Plants were pinched one time three weeks after planting and were 16 weeks old when the photograph and description were taken. In the following description, color references are made to The Royal Horticultural Society Colour Chart, 1995 Edition, except where general terms of ordinary dictionary significance are used.

Botanical classification: *Chamaesyce hypericifolia* 'Duestasufla'.

Parentage: Naturally-occurring whole plant mutation of a proprietary selection of *Chamaesyce hypericifolia* identified as code number EW09-0599-0030, not patented.

Propagation:

*Type.*—By vegetative cuttings.

*Time to initiate roots, summer.*—About five days at temperatures about 20° C.

*Time to initiate roots, winter.*—About seven days at temperatures about 20° C.

*Time to produce a rooted young plant, summer.*—About three weeks at temperatures about 20° C.

*Time to produce a rooted young plant, winter.*—About four weeks at temperatures about 20° C.

*Root description.*—Fine, fibrous; white in color.

*Rooting habit.*—Freely branching; dense.

Plant description:

*Plant and growth habit.*—Compact, upright, outwardly spreading and mounding plant habit; broad inverted triangle; moderately vigorous growth habit.

*Branching habit.*—Freely branching, usually about three to five primary branches each with numerous secondary and tertiary lateral branches developing per plant.

*Plant height.*—About 16 cm.

*Plant diameter.*—About 35 cm.

*Lateral branch description.*—Length: About 23.1 cm. Diameter: About 1.7 mm. Internode length: About 1.8 cm. Strength: Moderately strong. Texture: Smooth, glabrous. Color: Close to 146A.

Leaf description:

*Arrangement.*—Opposite; simple.

*Length.*—About 1.6 cm.

*Width.*—About 7.9 mm.

*Shape.*—Elliptical.

*Apex.*—Acute.

*Base.*—Attenuate to acute.

*Margin.*—Entire.

*Texture, upper surface.*—Pubescent.

*Texture, lower surface.*—Pubescent; rugose.

*Venation.*—Pinnate.

*Color.*—Developing leaves, upper surface: Close to 137A. Developing leaves, lower surface: Close to 137C. Fully developed leaves, upper surface: Close to 139A; venation, close to 137C. Fully developed leaves, lower surface: Close to 137C; venation, close to 137C.

*Petioles.*—Length: About 9.2 mm. Diameter: About 1 mm. Texture, upper and lower surfaces: Smooth, glabrous. Color, upper and lower surfaces: Close to 144A.

Inflorescence description: Inflorescence type and flowering habit: Relatively large inflorescences are compound corymbs of cyathia with white-colored flower bracts subtending the cyathia; inflorescences positioned above and beyond the foliar plane; freely flowering habit with hundreds of inflorescences per plant.

*Fragrance.*—None detected.

*Natural flowering season.*—Plants flower naturally during the spring and summer in Germany; inflorescence initiation and development can be induced under artificial long nyctoperiod conditions; early flowering habit, response time is about eight weeks under long nyctoperiod conditions.

*Post-production longevity.*—Inflorescences maintain good substance and bract color for about ten days; inflorescences persistent.

*Inflorescence diameter.*—About 2.9 cm.

*Inflorescence height (depth).*—About 1.9 cm.

*Flower bracts.*—Quantity per inflorescence: Two; opposite, fused at the base. Length: About 5.8 mm. Width: About 1.8 mm. Shape: Elliptic to lanceolate. Apex: Rounded to acute. Margin: Entire. Aspect: Mostly flat. Texture, upper and lower surfaces: Smooth, glabrous. Venation pattern: Pinnate. Color: Developing bracts, upper and lower surfaces: Close to 155D. Transitional bracts, upper and lower surfaces: Close to 155D. Fully developed bracts, upper and lower surfaces: Close to 155D; venation, close to 155D; color does not change with development. Bract petiole: Length: About 1.7 mm. Diameter: About 0.5 mm. Texture, upper and lower surfaces: Smooth, glabrous. Color, upper surface: Close to 146B to 146C. Color, lower surface: Close to 146B.

*Cyathia.*—Quantity per inflorescence: One. Length: About 4 mm. Width: About 0.75 mm. Shape: Ovoid. Texture: Smooth, glabrous. Color: Immature, inner and outer surfaces: Close to 144A. Mature, inner and outer surfaces: Close to 144A. Nectaries: Quantity per cyathium: Two. Length: About 1 mm. Diameter: About 1 mm. Shape: Ovoid. Color: Immature, inner and outer surfaces: Close to 146B and 155D. Mature, inner and outer surfaces: Close to 146B and 155D.

*Peduncles.*—Length: About 2.5 mm. Diameter: About 1 mm. Strength: Strong. Texture: Smooth, glabrous. Color: Close to 146A.

*Reproductive organs.*—Stamens: Quantity per cyathium: About four. Filament length: About 0.5 mm. Filament color: Close to 155D. Anther shape: Oval. Anther length: About 0.5 mm. Anther color: Close to 158C. Amount of pollen: Scarce. Pollen color: Close to 158D. Pistils: Quantity per cyathium: One. Pistil length: About 3 mm. Style length: About 0.5 mm. Style color: Close to 155D. Stigma shape: Crested. Stigma color: Close to 155D. Ovary color: Close to 144A. Seeds and fruits: Seed and fruit production have not been observed on plants of the new *Euphorbia*.

Temperature tolerance: Plants of the new *Euphorbia* have been observed to tolerate temperatures ranging from about 5° C. to about 40° C.

Pathogen & pest resistance: Plants of the new *Euphorbia* have not been observed to be resistant to pathogens and pests common to *Euphorbia* plants.

It is claimed:

1. A new and distinct *Euphorbia* plant named 'Duestasufla' as illustrated and described.

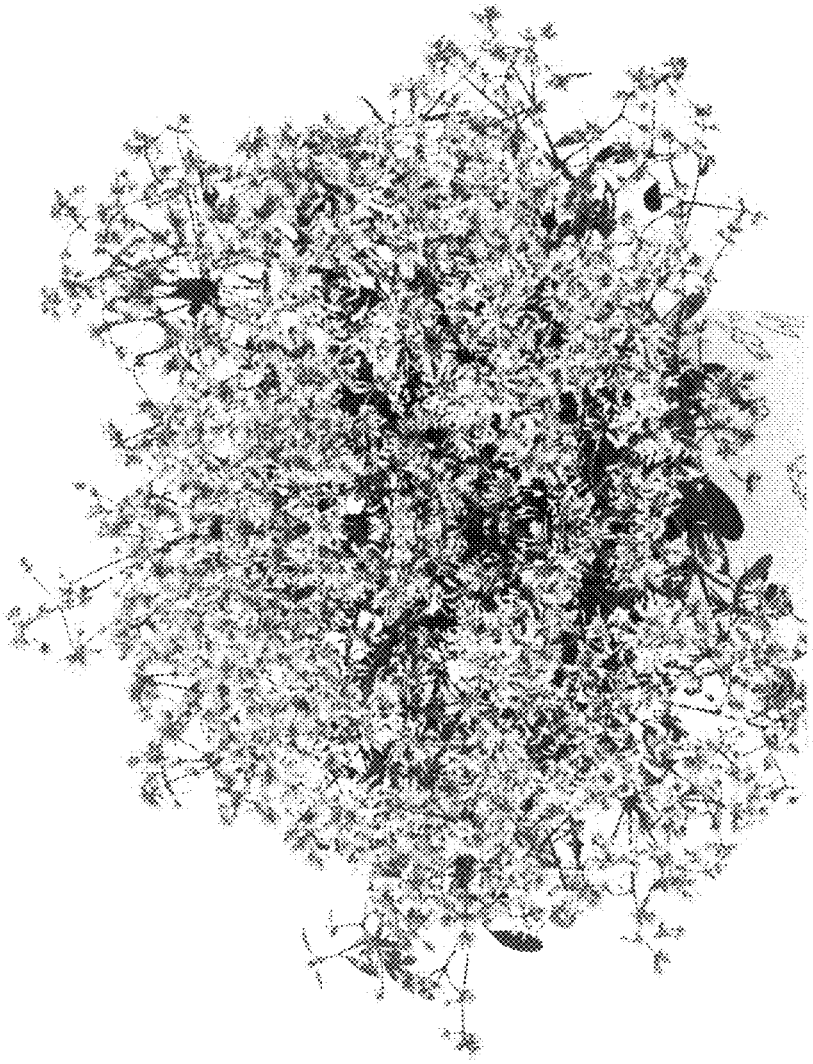

* * * * *